United States Patent [19]
Long et al.

[11] Patent Number: 6,087,531
[45] Date of Patent: Jul. 11, 2000

[54] PROCESS FOR THE RECOVERY OF NAPHTHALENEDICARBOXYLIC ACID FROM POLY (ALKYLENE NAPHTHALENEDICARBOXYLATE)

[75] Inventors: Timothy Edward Long, Blountville; Phillip Montgomery Hudnall; James Rodney Bradley, both of Kingsport, all of Tenn.

[73] Assignee: Eastman Chemical Company, Kingsport, Tenn.

[21] Appl. No.: 09/100,746

[22] Filed: Jun. 19, 1998

Related U.S. Application Data

[60] Provisional application No. 60/051,354, Jun. 30, 1997.
[51] Int. Cl.[7] .................................................. C07C 51/42
[52] U.S. Cl. .............................................................. 562/485
[58] Field of Search ..................................... 562/485, 486, 562/487

[56] References Cited

U.S. PATENT DOCUMENTS

| | | |
|---|---|---|
| 4,355,175 | 10/1982 | Pusztaszeri ............................... 562/483 |
| 5,414,113 | 5/1995 | Broeker et al. . |
| 5,473,102 | 12/1995 | Johnson et al. . |

FOREIGN PATENT DOCUMENTS 0 712 832   5/1996   European Pat. Off. .

*Primary Examiner*—Samuel Barts
*Attorney, Agent, or Firm*—B. J. Boshears; Harry J. Gwinnell

[57] ABSTRACT

Disclosed is a process for the recovery of naphthalenedicarboxylic acid (NDA) from polyester materials prepared from and/or containing residues of NDA such as a poly(alkylene naphthalenedicarboxylate). In one embodiment, the process comprises contacting a polyester material prepared from and/or containing residues of NDA with water at a temperature of about 125 to 400° C. in a pressured vessel to obtain an aqueous slurry of NDA and recovering the NDA. A second embodiment of the process comprises contacting such a polyester with an aqueous, alkali metal base solution to obtain an aqueous solution of a di-alkali metal naphthalenedicarboxylate salt, then neutralizing the aqueous solution with an acid to obtain an aqueous slurry or dispersion of NDA and recovering the NDA. The process is particularly useful for recovering 2,6-naphthalenedicarboxylic acid (2,6-NDA) from poly(ethylene naphthalenedicarboxylate) polyesters.

6 Claims, No Drawings

PROCESS FOR THE RECOVERY OF NAPHTHALENEDICARBOXYLIC ACID FROM POLY (ALKYLENE NAPHTHALENEDICARBOXYLATE)

CROSS REFERENCES TO RELATED APPLICATION

This application claims the benefit of United States Provisional Application Serial No. 60/051,354 filed Jun. 30, 1997.

FIELD OF THE INVENTION

This invention pertains to a process for the recovery of naphthalenedicarboxylic acid (NDA) from polyester materials prepared from and/or containing residues of NDA. More specifically, this invention pertains to a process for the recovery of NDA from polyesters containing NDA residues by contacting such a polyester with water at a temperature of about 125 to 400° C. in a pressured vessel to obtain an aqueous slurry of NDA and recovering the NDA. A second embodiment of the present invention pertains to a process for the recovery of NDA from polyesters containing NDA residues by contacting such a polyester with an aqueous, alkali metal base solution to obtain an aqueous solution of a di-alkali metal naphthalenedicarboxylate salt, then neutralizing the aqueous solution with an acid to obtain an aqueous slurry or dispersion of NDA and recovering the NDA. The polyester utilized in the process may be a poly(alkylene naphthalenedicarboxylate). The process is particularly useful for recovering 2,6-naphthalenedicarboxylic acid (2,6-NDA) from poly(ethylene naphthalenedicarboxylate) polyesters.

BACKGROUND OF THE INVENTION

It is well known in the literature that the presence of naphthalene moieties or residues (typically derived from a NDA or diester monomer) in polyesters imparts increased barrier performance and thermo-oxidative stability. Both of these attributes are important for polyesters which are used in packaging various beverages including water, carbonated soft drinks, and beer. In addition, naphthalene residues are particularly useful in certain polyesters such a liquid crystalline polymers due to the formation of a sideways displacement in the polymer backbone that imparts processability to high temperature polymers including liquid crystalline polymers without a significant reduction in the level of three-dimensional crystallinity. High levels of crystallinity result in higher heat distortion temperatures that are essential in many applications such as heat stable containers, electrical connectors, automotive applications, and computer hardware.

Although polyesters derived from NDA such a poly (alkylene naphthalenedicarboxylate) have been known in the literature for many years, the commercial availability of such a polyester, poly(ethylene 2,6-naphthalenedicarboxylate) (PEN) is a relatively recent event. PEN possesses a higher glass transition temperature ($T_g$), e.g., 125° C., compared to the $T_g$ poly(ethylene terephthalate) (PET), e.g. 80° C. In addition, it is well known that the barrier to oxygen exhibited by PEN is five times greater than that exhibited by PET. As a result, it is expected that PEN will experience increased use in beverage container applications and high performance film applications. Due to the desirability of plastic recycling, the conversion of used or waste PEN polyester polymer to useful materials, especially 2,6-NDA, is a particularly important and desirable objective.

Processes for the recovery of naphthalene moieties or residues from poly(alkylene naphthalenedicarboxylates) polyesters are known. For example, Published PCT Patent Application WO 8911471 describes the formation and recovery of dialkyl 2,6-naphthalenedicarboxylates from poly (alkylene 2,6-naphthalenedicarboxylates) polyester polymers. The process described involves the use of an alcoholic solvent in the presence of a transesterification catalyst. U.S. Pat. No. 5,414,113 describes the recovery and purification of aromatic dicarboxylic acids from waste polyester film, fiber, bottles, and manufacturing residues. The process comprises the depolymerization of polyester resin in a solvent followed by an oxidative purification step. U.S. Pat. No. 5,473,102 discloses a process comprising depolymerization of a polyester resin in a molten polyester resin containing solvent with superheated steam followed by high temperature distillation of the dicarboxylic acid monomer for purification.

BRIEF SUMMARY OF THE INVENTION

The present invention provides a process for recovering a naphthalenedicarboxylic acid (NDA) from polyester materials prepared from and/or containing residues of NDA. In its broadest aspect, the process comprises first contacting a polyester containing NDA residues with water at a temperature of about 125 to 400° C. to obtain an aqueous slurry of NDA and then recovering the NDA. A second embodiment of the process comprises the steps of:

(1) contacting a polyester containing naphthalenedicarboxylic acid (NDA) residues, e.g., a poly(alkylene naphthalenedicarboxylate), with an aqueous, alkali metal base solution to obtain an aqueous solution of a di-alkali metal naphthalenedicarboxylate salt;

(2) neutralizing the aqueous solution with an acid to obtain an aqueous slurry or dispersion of NDA; and (3) recovering the NDA.

As mentioned hereinbefore, the process is particularly useful for recovering 2,6-naphthalenedicarboxylic acid (2,6-NDA) from poly(ethylene naphthalenedicarboxylate) polyesters. The process is simple to operate to obtain NDA in high yields and excellent purity for use in subsequent polyesterification and acidolysis processes for the manufacture of polyesters.

The NDA which may be recovered in accordance with the present invention is useful for preparing a variety of known polyesters such as PEN and liquid crystalline polyesters. Polyesters containing residues of NDA have been prepared from the commercially-available, dimethyl naphthalenedicarboxylate (DMN) monomer. The dimethyl ester often is not the monomer of choice for the introduction of the naphthalene unit into a polyester polymer backbone. Polyester polymers prepared via the dicarboxylic acid-based monomer often exhibit superior thermal stability and improved color due to the absence of residues of transesterification catalysts required when a diester of NDA is employed in the synthesis of such polymers. In addition, many synthetic methodologies and manufacturing processes are not compatible with the diester monomer. For example, liquid crystalline polyesters typically are prepared by means of an acidolysis reaction that requires the presence of carboxylic acid reactive groups. In some instances, the diester monomer leads to undesirable branching and degradation chemistries when exposed to the acidolysis reaction conditions. Furthermore, the preparation of polyesters using dicarboxylic acid monomers as opposed to the corresponding dimethyl esters may produce a polymer containing less acetaldehyde, a degradation byproduct of ethylene glycol based polyesters.

DETAILED DESCRIPTION OF THE INVENTION

In the first embodiment of the process of the present invention, a polyester containing NDA residues, e.g., polyester-forming residues having the general formula

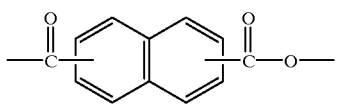

Is dispersed and heated in water under autoclave conditions. The concentration of the polyester slurried in water typically is in the range of 1 to 50 weight percent, preferably about 10 to 20 weight percent. The process is carried out at elevated temperatures in the range of about 125 to 400° C., preferably in the range of about 170 to 240° C. When the hydrolysis is complete, the NDA may be recovered from the resulting slurry of NDA by filtration, e.g., at 70° C., by filtration and washed with water. This slurry typically is thick and difficult to handle. The potential corrosivity of the reaction medium at elevated temperatures dictates that the equipment used be fabricated from high corrosion-resistant materials of construction.

Because of the insolubility and uncontrolled crystallization of NDA under the process conditions employed in the first embodiment of the present process, the purity of the NDA product is less than may be desired. Numerous unidentified low boiling and high boiling impurities may total from about 1.8 to 3.5 weight percent on the recovered NDA. Furthermore, the presence of up to 260 ppm Fe, 43 ppm Ni and 19 ppm Cr are evidence of significant corrosion in the laboratory autoclave.

In the second and preferred embodiment of our invention, a polyester containing NDA residues is dispersed and heated in an aqueous solution of an alkali metal base. The particular polyester used in the process is not critical and can be a poly(ethylene naphthalenedicarboxylate) composed of residues from a single glycol or diol and a single dicarboxylate monomer. Alternatively, the polyester can contain the residues of a plurality of diols and/or a plurality of dicarboxylate monomers, e.g., a liquid crystalline polyester comprising residues of 2,6-naphthalenedicarboxylic acid, terephthalic acid, hydroquinone, 4-hydroxybenzoic acid, and, optionally, 4,4'-biphenol. The polyester may have an inherent viscosity (IV) in the range of about 3 to 10 dL/g measured in 70:30 by weight mixture of pentafluorophenol and trichlorobenzene. The polyester polymer preferably is poly(ethylene naphthalenedicarboxylate). However, other polyesters derived from a naphthalenedicarboxylic acid and one or more other diols, e.g., 1,4-butanediol and 1,4-cyclohexanedimethanol, may be used. Hydrolysis of the polyester polymer and saponification of the NDA residues is facilitated if the polyester used has first been reduced in size, e.g., by shredding, grinding, pelletizing, grinding, etc., to give relatively small and/or thin particles or pieces of polyester.

The base utilized in step (1) may be selected from the hydroxides and carbonates of the alkali metals, preferably sodium or potassium, and most preferably sodium hydroxide. The minimum of alkali metal base required is two equivalents of base per equivalent of naphthalenedicarboxylate residue (plus and other carboxylate or dicarboxylate residues) present in the polyester employed. We have found that the mono-alkali metal salt of NDA is sparingly soluble in water. Thus, to achieve complete dissolution, sufficient alkali metal base must be used to convert essentially all of the NDA residues to the di-alkali metal salt. Because of equilibria and solubility considerations, and dependent upon the amount of base used, the solubilized NDA may contain some mono-alkali metal salt under certain conditions. Excess base is neither necessary nor detrimental to the operation of the process.

The first step of the three-step process is carried out at elevated temperatures in the range of about 125 to 400° C., preferably at about 170 to 240° C. The first step is performed under the autogenous pressure generated by the temperature chosen. The concentration of the polyester in the polyester-:water slurry may be about 1 to 50 weight percent but preferably is in the range of about 10 to 20 weight percent. Normally, the duration of the first step is determined by the time required to effect substantial dissolution of the starting polyester material resulting from hydrolysis of all or substantially all of the ester linkages present in the polyester. At the conclusion of step (1), all, or essentially all, of the naphthalenedicarboxylic acid residues present in the polyester starting material have been converted to the di-alkali metal naphthalenedicarboxylate, e.g., disodium naphthalenedicarboxylate.

In the second step of the process, the solution of the di-alkali metal naphthalenedicarboxylate salt in water is treated with an acid to convert the salt to NDA. The acid used may be selected from essentially any inorganic or organic acid such as, for example, the hydrohalide acids, sulfuric acid, phosphoric acid, an organic sulfonic acid, e.g., methanesulfonic, benzenesulfonic and toluenesulfonic acids, carboxylic acids, e.g., acetic acid, and the like. The preferred acid is acetic acid since the salt of neutralization (an alkali metal acetate, e.g., sodium acetate) is very water-soluble and is more easily washed from the isolated NDA. The quantity of acid must be sufficient to neutralize the NDA salts and any excess base completely. Preferably, a two-fold molar excess is used to ensure complete conversion of the di-alkali metal salt to NDA.

The temperature at which the second step is performed is not critical and is limited only by practical constraints. Thus, step (2) may be carried out at temperatures in the range of about 0 to 250° C. although temperatures in the range of about 50 to 90° C. are more practical and thus preferred. In the third step, the NDA may be recovered by conventional liquid/solid separation procedures such as filtration or centrifugation, usually with washing or reslurrying with water. In a preferred embodiment, the second and third steps are carried out at approximately 70° C. The recovered NDA typically is dried. The process of our invention typically gives a recovery yield exceeding 95% and a NDA having a purity greater than 99%.

The NDA produced by the process of the invention is particularly suited for use in the preparation of liquid crystalling polyesters via melt acidolysis procedures using at least one monomer containing acetoxy groups, e.g., 1,4-diacetoxybenzene and 4-acetoxybenzoic acid. The alkali metal salt generated in the second step of the process may be useful as a catalyst for acidolysis chemistry. Thus, it is possible that the presence of some salt by-product, e.g., sodium acetate, in the NDA may serve as a subsequent polymerization catalyst wherein the NDA is reacted with other monomers to produce a polyester polymer.

The use of water as medium in the present process provides a plurality of advantages including an essentially pure NDA product, a low cost and no hazard or safety concerns as compared to known processes for the recovery of NDA. The NDA product obtained from the process is sufficiently pure that no purification treatment or process is required resulting in a lower cost product.

The processes of our invention are further illustrated by the following examples. The depolymerization/hydrolysis portion of the processes was carried out in a conventional 500 mL laboratory autoclave constructed of 316 stainless steel and equipped with a magnetically-driven internal agitator. The acidification and workup portions of the processes were carried out in glass equipment. The polyester used in the examples was poly(ethylene 2,6-naphthalenedicarboxylic acid (PEN) having an IV of 0.56 dL/g measured in 70:30 by weight mixture of pentafluorophenol and trichlorobenzene in the form of pellets about 2 by 4 mm in size. Analyses for NDA were carried out by gas chromatography and for sodium and corrosion metals by the inductively coupled plasma analytical technique.

EXAMPLE 1

PEN (50 g) was dispersed in water (300 g) and 50 weight percent aqueous sodium hydroxide solution (33 g) was added. The mixture then was heated to 200° C. in an autoclave and maintained at this temperature for 2.5 hours. The resulting homogeneous solution was acidified with acetic acid (50 g) at 70° C. for 1 hour, and 500 g of additional water was added and the white precipitate was filtered at 70° C. The product was washed thoroughly with 750 g of water at 70° C. After drying at 100° C. to remove residual water, the yield of recovered NDA was determined to be 93.8% and the purity was 99.13%. The NDA product contained 49 ppm sodium and no detectable corrosion metals.

EXAMPLE 2

PEN (50 g) was dispersed in water (300 g) of water and 50 weight percent aqueous sodium hydroxide solution (40 g) was added to the dispersion. The mixture was heated to 200° C. and maintained at this temperature for 4.0 hours. The resulting homogeneous solution was acidified with acetic acid (55 g) at 70° C. for 1 hour, and 500 g of additional water was added. The white precipitate was filtered at 70° C. The product was washed thoroughly with 750 grams of water at 70° C. After drying at 100° C. to remove residual water, the yield of recovered NDA was 95.8% and the NDA had a purity of 100.0%. The NDA product contained 51 ppm sodium and no detectable corrosion metals.

EXAMPLE 3

PEN (50 g) was dispersed in water (300 g) and 50 weight percent aqueous sodium hydroxide solution (40 g) was added to the dispersion. The resulting mixture was heated to 240° C. and maintained at this temperature for 4.0 hours. The resulting homogeneous solution was acidified with 55 grams of acetic acid at 70° C. for 1 hour, and 300 g of additional water was added. The white precipitate was filtered at 70° C. The NDA product was washed thoroughly with 500 g of water at 70° C. After drying at 100° C. to remove residual water, the yield of recovered NDA was 95.0% and the NDA had a purity of 99.64%. The NDA product contained 972 ppm sodium and no detectable corrosion metals.

Comparative Example 1

PEN (50 g) was dispersed in water (225 g) and 50 weight percent sodium hydroxide solution (40 g) was added. The mixture was heated to 100° C. and maintained at this temperature for 20 hours. No reaction occurred.

EXAMPLE 4

PEN (50 g) was dispersed into water (300 g) and the dispersion was heated for 4.0 hours at 240° C. in the absence of base. The resulting thick slurry of off-white crystals was accompanied by coating of the vessel walls. The thick slurry was filtered at 70° C., washed with water, and then dried at 100° C. to remove residual water. The recovered NDA had a purity of 98.12% and contained the following corrosion metals: 259 ppm iron, 43 ppm nickel and 19 ppm chromium.

EXAMPLE 5

A NDA product containing 450 ppm sodium and prepared as described in Example 3 was reslurried in water and filtered. The washed product contained only 24 ppm of sodium metal.

Utility Example 1

This example illustrates the preparation of a liquid crystalline polyester consisting of 12 mole percent terephthalic acid residues, 28 mole percent 2,6-naphthalenedicarboxylic acid (NDA) residues, 40 mole percent hydroquinone residues, and 60 mole percent p-hydroxybenzoic acid residues using an in situ acetylation monomer acidolysis route. The NDA utilized was obtained from the process described in Example 3 and contained 972 ppm sodium.

The following monomers were placed in a 500 mL flask equipped with an inlet for nitrogen, a metal stirrer, and a short distillation column:

| | |
|---|---|
| Terephthalic acid | 5.0 g; 0.03 mole |
| 2,6-Naphthalenedicarboxylic acid | 15.1 g; 0.07 mole |
| Hydroquinone | 12.1 g; 0.11 mole; 10% molar excess |
| p-Hydroxybenzoic acid | 20.7 g; 0.15 mole |

The flask was degassed three times with a nitrogen-vacuum cycle, and finally released to nitrogen. After degassing, acetic acid (30 mL) and acetic anhydride (41.5 g; 38.4 mL; 0.407 mole) were added. The flask was placed in a Belmont metal bath at 135° C. and the contents of the flask were heated at 135° C. for approximately 3 hours. The temperature was raised gradually to 280° C. over a 30-minute period, and maintained for one hour at 280° C., one hour at 300° C., and one hour at 320° C. The temperature was raised to 350° C. and vacuum was gradually applied over a 15-minute period to a pressure of 0.5 Torr. The reaction was allowed to proceed at 0.5 Torr for 30 minutes. The liquid crystalline polyester thus obtained had an IV of 8.1 dL/g determined by dissolving a sample of the polyester (0.1 weight %) in a 60:40 by weight mixture of pentafluorophenol and trichlorobenzene at ambient temperature (approximately 24 hours typically were required to form a clear solution). The polyester also had a number average molecular weight ($M_n$) of 13,200 and a weight average molecular weight ($M_w$) of 64,900 as determined by gel permeation chromatography, a $M_z/M_n$ value of 11.3, a first melting point of 326° C. and a second melting point of 325° C. determined by differential scanning calorimetry and a $T_{cc}$ of 291° C.

The invention has been described in detail with particular reference to preferred embodiments thereof, but it will be understood that variations and modifications can be effected within the spirit and scope of the invention.

We claim:

1. Process for recovering a naphthalenedicarboxylic acid (NDA) from polyester materials prepared from and/or containing residues of NDA comprising the steps of:
    (1) contacting a polyester containing naphthalenedicarboxylic acid (NDA) residues with an aqueous, basic solution at a temperature of about 125 to 400° C. to obtain an aqueous solution of a dialkali metal naphthalenedicarboxylate salt;
    (2) neutralizing the aqueous solution with an acid to obtain an aqueous slurry of NDA; and
    (3) recovering the NDA.

2. Process according to claim 1 wherein the aqueous basic solution is an aqueous alkali metal base solution.

3. Process according to claim 1 wherein the polyester is a poly(alkylenenaphthalenedicarboxylate) and the base is a hydroxide or carbonate of an alkali metal.

4. Process according to claim 1 wherein the acid used in step (2) is a carboxylic acid.

5. Process according to claim 4 wherein step (1) is carried out at a temperature of about 170 to 240° C. and the acid used in step (2) is acetic acid.

6. Process for recovering 2,6-naphthalenedicarboxylic acid (NDA) from poly(ethylene dicarboxylate) comprising the steps of:
    (1) contacting poly(ethylene dicarboxylate) with an aqueous solution of sodium or potassium hydroxide at a temperature of about 170 to 240° C. to obtain an aqueous solution of a di-sodium or di-potassium 2,6-naphthalenedicarboxylate;
    (2) neutralizing the aqueous solution with acetic acid to obtain an aqueous slurry of NDA; and
    (3) recovering the NDA.

* * * * *